(12) United States Patent  (10) Patent No.: US 8,545,465 B2
Daly et al.  (45) Date of Patent: Oct. 1, 2013

(54) MEDICAL DRAINAGE DEVICE AND A FILL FUNNEL FOR A MEDICAL DRAINAGE DEVICE

(75) Inventors: Paul J. Daly, Tullamore (IE); David Rork Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 884 days.

(21) Appl. No.: 12/623,504

(22) Filed: Nov. 23, 2009

(65) Prior Publication Data

US 2010/0130948 A1  May 27, 2010

(30) Foreign Application Priority Data

Nov. 26, 2008 (EP) .................................... 08169982

(51) Int. Cl.
*A61M 1/00* (2006.01)
(52) U.S. Cl.
USPC ............................. 604/317; 604/313; 604/319

(58) Field of Classification Search
USPC .................................................. 604/313, 319
See application file for complete search history.

(56) References Cited

U.S. PATENT DOCUMENTS

| 3,782,497 A | 1/1974 | Bidwell et al. |
| 6,155,315 A | 12/2000 | Peterson |
| 2002/0072722 A1 | 6/2002 | Swisher et al. |
| 2002/0198505 A1 | 12/2002 | Want et al. |

FOREIGN PATENT DOCUMENTS

GB  2 077 600 A  12/1981

OTHER PUBLICATIONS

European Search Report for Appln. No. 08 16 9982 completed Apr. 9, 2009.

*Primary Examiner* — Melanie Hand

(57) ABSTRACT

A medical drainage device is provided which includes a casing and a chamber for indicating the amount of suction applied to an animal or human body by the height of a water column. A fill funnel is further provided, which is attached to an opening in the casing for filling water through the opening into the chamber. The fill funnel has a configuration rendering the fill funnel selectively impermeable. A fill funnel and a method of manufacturing a fill funnel are also provided.

17 Claims, 4 Drawing Sheets

MEDICAL DRAINAGE DEVICE AND A FILL FUNNEL FOR A MEDICAL DRAINAGE DEVICE

TECHNICAL FIELD

The present disclosure relates to a medical drainage device and to a fill funnel for a medical drainage device.

BACKGROUND

The clinical need for chest drainage arises anytime the negative pressure in the pleural cavity is disrupted by the presence of air and/or fluid resulting in pulmonary compromise. The purpose of a chest drainage device is to evacuate the air and/or fluid from the chest cavity to help re-establish normal intrathoracic pressure. This facilitates the re-expansion of the lungs to restore normal briefing dynamics. The need also arises following heart surgery to prevent the accumulation of fluid around the heart.

FIG. 1 shows a conventional medical drainage device 1, which is used for a chest drainage. The medical drainage device 1 includes a casing 11 and attached to the casing includes a patient drain catheter 12. This in turn is connected to either a thoracic or trocar catheter. Patients with continual air or fluid leaks have such a thoracic catheter, also called chest tube, inserted. The distal end of the catheter, which will be inside the patient's chest, has a number of drainage holes. The last inlet can be detected on a chest X-ray as intermittent breaks in a radiopaque line. Once the chest tube has been properly positioned and secured, the X-ray should be checked to ensure that all drainage holes are inside the chest wall.

The location of the chest tube depends on what is being drained. Free air in the pleural space rises, so the tube is placed above the second intercostal space at the mid-clavicular line. Plural fluid gravitates to the most dependent point, so the tube is placed at the fourth to fifth intercostal space along the mid-axillary line. Mediastinal tubes placed to drain the pericardium after open-heart surgery are positioned directly under the sternum. Once the chest tube is in place, it is connected to a medical drainage device 1, usually called chest drainage unit (CDU) via the patient drain catheter 12.

The patient drain catheter 12 is directly connected to a collection chamber 14 of the medical drainage device 1 and any drainage from the chest flows into this collection chamber 14. The collection chamber 14 is graduated to provide an assessment and has a write-on surface to allow for recording of the time, date and amount of drainage.

The medical drainage device 1 further includes a chamber 15 which in traditional medical drainage devices is the water seal area. The main purpose of the water seal is to allow air to exit from the pleural space on exhalation and prevent air from entering the plural cavity or mediastinum on inhalation.

The medical drainage device 1 further includes a suction control regulator. The amount of suction, i.e. of negative pressure, applied to the patient's body is indicated by the height 18 of water 17 on a graduated scale. This is called the Patient Assessment manometer. A suction pressure of between 15-20 cm $H_2O$ is commonly recommended. Lower levels may be indicated for infants and for patients with friable lung tissue or if ordered by the physician. These medical drainage devices are normally stationary either by placing them on the floor or hanging them on the bed rail below the chest.

When a medical drainage device 1 is being prepared for the use, sterile water is filled into both the water seal chamber 15 and the patient assessment manometer chamber 16 until it reaches the fill lines. The patient assessment manometer provides an assessment of negative pressure within the collection chamber and patient chest. This is accomplished by a true U tube water manometer design in the medical drainage device which indicates patient intrapleural pressure. At the bottom of this manometer chamber 16 there is a dyeing device 13, usually a die ball, which dies the water, e.g. blue, which makes it easier for the nurse and/or the physician to see the suction level applied to the patient i.e. the water height 18. The dyeing device 13 floats around freely at the bottom of this chamber 16.

During the preparation and setup of the medical drainage device 1 an instruction tape is removed from the opening 19. It is into this opening 19 that the sterile water is poured to fill the patient assessment manometer to the required level.

The problems that arise with such a medical drainage device are that there is a risk that the dyeing device 13 falls out of the patient assessment manometer chamber 16 through the opening 19. Additionally, when the water is filled through the opening 19 into this chamber 16, it is quite difficult since the opening 19 usually is very small and therefore a lot of water will fall outside the hole 19.

It is therefore an object of the present disclosure to reduce the disadvantages of the prior art.

SUMMARY

Fill in when claims are finalized

BRIEF DESCRIPTION OF FIGURES

Various embodiments of the present disclosure will be described herein below with reference to the figures wherein.

DETAILED DESCRIPTION

The present disclosure provides a medical drainage device, a fill funnel and a method of manufacturing a fill funnel.

In embodiments, the present disclosure provides a medical drainage device including: a casing, and a chamber for indicating the amount of suction applied to an animal or human body by the height of a water column. A fill funnel may be attached to an opening in the casing for filling water through the opening into the chamber, wherein the fill funnel has a configuration rendering the fill funnel selectively impermeable.

In embodiments, the present disclosure further provides a fill funnel for a medical drainage device, the fill funnel being attachable to an opening in the casing of a medical drainage device for enabling to fill water through the opening into a chamber, and the fill funnel having a configuration rendering the fill funnel selectively impermeable.

In embodiments, the present disclosure further provides a method of manufacturing a fill funnel for a medical drainage device, which includes the steps of providing a fill funnel being attachable to an opening in the casing of a medical drainage device for enabling to fill water through the opening into chamber and providing a configuration of the fill funnel rendering the fill funnel selectively impermeable.

In embodiments, the fill funnel may have a configuration rendering the fill funnel impermeable to components and/or particles exceeding a predefined size.

In embodiments, the fill funnel may have a configuration rendering the fill funnel permeable to gas and liquid.

In one embodiment, the fill funnel may include a blocking device for rendering the fill funnel selectively impermeable.

In embodiments, the blocking device may be a cloth. Alternatively, the blocking device may include means for reducing the inner size and/or the diameter of the fill funnel. In embodiments, the blocking device may be a bar across the inner side of the fill funnel, a cross within the fill funnel or at least one bar, in embodiments, a circumferential bar, protruding from the inner walls of the fill funnel. In embodiments, the fill funnel may be flush with the casing.

In one embodiment, the fill funnel may be at least partly inserted into the opening. Alternatively, the fill funnel may be imposed on connection means protruding from the casing around the opening.

In embodiments, fixation means may be provided for fixedly attaching the fill funnel to the casing.

In an embodiment, the chamber may be a patient assessment manometer chamber.

In embodiments, the fill funnel may be attached to the medical drainage device by means of a string.

The present disclosure will now be explained in more detail in the following description of embodiments in relation to the figures.

Figure 1:
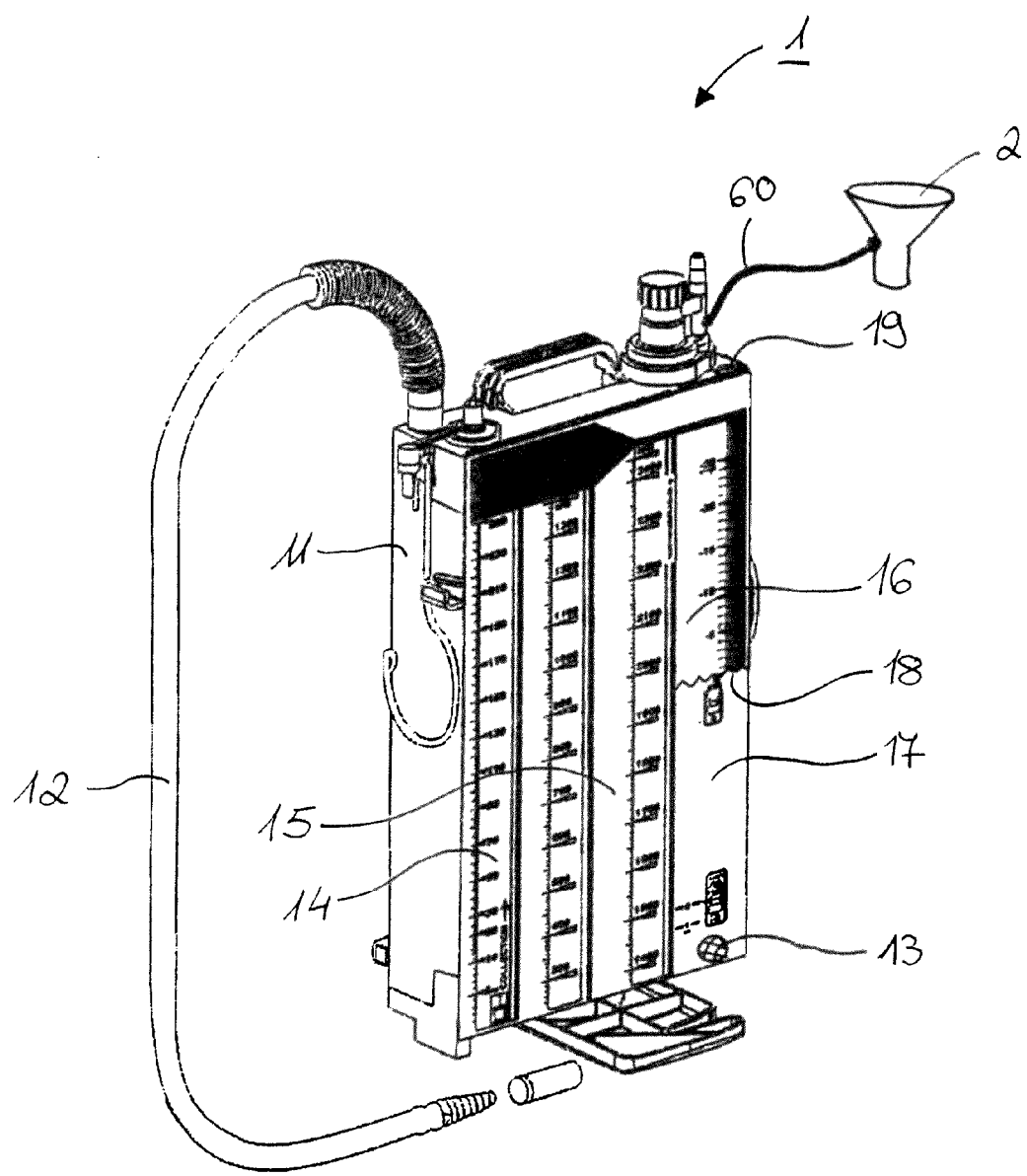
FIG. 1 shows a medical drainage device in accordance with the present disclosure.
Figure 2:
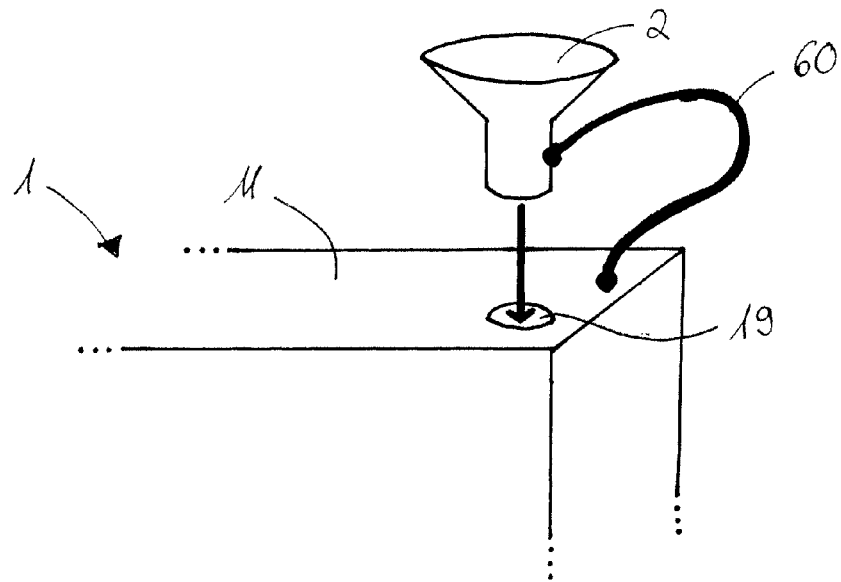
FIG. 2 shows a schematic drawing of a medical drainage device with a fill funnel according to the present disclosure.

The present disclosure refers to a medical drainage device 1 used for draining air and/or fluid from a patient's body. An example of such a medical drainage device 1 of the prior art is shown in FIG. 1 and is described above. The present disclosure is not limited to a medical drainage device 1 as shown in FIG. 2 but can be used with any other type of medical drainage device having different shapes and/or configurations.

The medical drainage device according to the present disclosure includes a casing 11 and a chamber 16 for indicating the amount of suction applied to an animal or human body, i.e. the amount of suction applied to the pleural space, by the height 18 of a water column. Further, a dyeing device 13 is provided in the chamber 16 for dyeing the water therein. The dyeing device 13 can be, for example, a dyeing ball, and the water can be, for example, coloured in blue so as to facilitate the recognition of the water height within the 16. When the medical drainage device 1 is prepared for use, then the dyeing device 13 and afterwards the water 17 is filled through the opening 19 into the chamber 16. In embodiments, the chamber 16 is a patient assessment manometer chamber 16.

According to an embodiment of the present disclosure, a medical drainage device 1 is provided having a fill funnel 2 attached to the opening 19 in the casing 11 for filling water through the opening 19 into the chamber 16. This is schematically shown in the drawing in FIG. 2. FIG. 2 shows a part of the casing 11 of the medical drainage device 1 having opening 19 therein. The fill funnel 2 is attached to the opening, which is indicated by an arrow in FIG. 2. The present disclosure therefore proposes a medical drainage device, with a simple and more secure means to fill water 17 through the opening 19 into the chamber 16. The fill funnel 2 attached to the opening 19 allows it to easily fill water into the chamber 16 without water falling outside the opening 19.

Further, according to the present disclosure, the fill funnel 2 has a configuration, rendering the fill funnel selectively impermeable, i.e. a configuration which allows to select specific components and/or particles which are not able to pass through the fill funnel 2. The fill funnel 2 has a configuration rendering the fill funnel 2 impermeable to components and/or particles exceeding a predefined size or particle size.

In order to enable to fill water 17 through the fill funnel 2 into the chamber 16, the fill funnel is permeable to water, more generally to liquids. Further, since air is removed out of the chamber 16 when the water is filled in and since the pressure within the chamber 16 is adjusted during the use of the medical drainage device 1, the fill funnel is also permeable to air, more generally to gas.

It is hereby noted, that the permeability or impermeability is not intended to relate to the material out of which the fill funnel 2 is made but rather relates to the configuration of the fill funnel 2, i.e. to the shape of the fill funnel 2 itself and to the shape of components being part of the fill funnel 2 and to the relative position of the components of the fill funnel 2.

In embodiments, the fill funnel 2 is configured in such a way, that it is impermeable to the dyeing device 13. That means that the fill funnel either prevents the dyeing device 13 from leaving the chamber 16 or in any case prevents the dyeing device 13 from leaving the fill funnel 2. Thereby, if the medical drainage device 1 falls down or is held in a wrong position, the dyeing device 13 slides or falls back into the chamber 16, since the fill funnel 2 due to the configuration stops the dyeing device 13 from passing the fill funnel 2 and thereby from getting lost.

As shown in FIGS. 1 and 2, the fill funnel 2 can be attached to the medical drainage device 1 by a string 60. The string 60 prevents the fill funnel 2 from dropping or getting lost. On the other hand, the string 60 is long enough and flexible enough to enable the insertion of the fill funnel 2 into the opening 19 of the casing 11.

FIGS. 3a to 3d show different embodiments of a shape of a fill funnel 2 according to the present disclosure. The fill funnel 2 has a diameter and/or size which increases with increasing distance from the opening 19, when the fill funnel 2 is attached to the opening 19. Therefore, the fill funnel 2 has the smallest diameter and/or the smallest size in the vicinity of the opening and with increasing distance from the opening, the size and/or the diameter of the fill funnel 2 increases.

In the following description, a reference to the "top" of a fill funnel 2, is intended to refer to the part of the fill funnel 2, where water is filled in, and a reference to the "bottom" of the fill funnel 2 is intended to refer to the part of the fill funnel 2, where the water comes out.

Figure 3A:
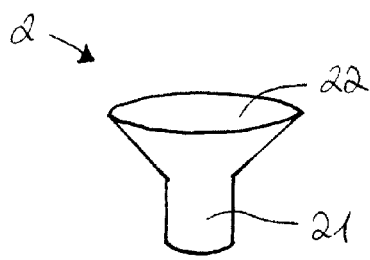
FIGS. 3a to 3d show schematic drawings of different embodiments of a fill funnel according to the present disclosure.
Figure 3B:
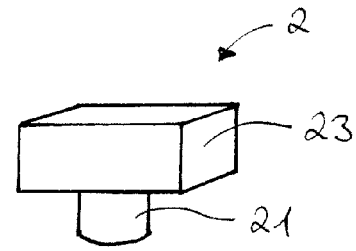
Figure 3C:
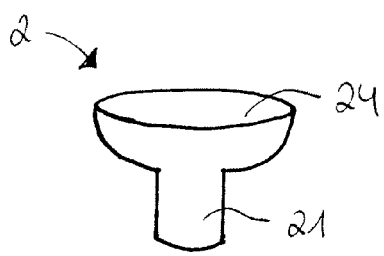
Figure 3D:
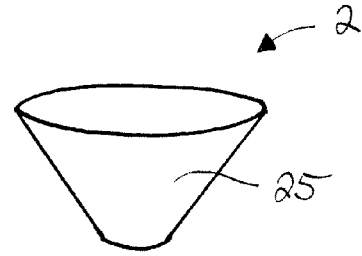

FIGS. 3a to 3c show a fill funnel, which has a cylindrical bottom part 21 with different types of top parts attached thereto. In FIG. 3a, the top part is a truncated cone 22, the top part shown in FIG. 3b is a cuboid 23, and the top part shown in FIG. 3c is a paraboloid of revolution 24. Depending on the way the fill funnel 2 is attached to the opening 19, the fill funnel can also consist of one single part, which is for example shown in FIG. 3d, where the fill funnel 2 is a truncated cone 25.

The present disclosure is not limited to the above shown embodiments of a fill funnel 2. The fill funnel can consist of one, two or more parts and each of these parts can have a circular, oval, elliptical, rectangular or any other cross-section and can be constant in size or can be increasing in size. The top of the fill funnel 2 is larger in size and/or diameter than the bottom part of the fill funnel 2, so that more water or any other fluid can pass through the top than through the bottom of the fill funnel.

The specific configuration of the fill funnel 2 for rendering the fill funnel 2 selectively impermeable will be described in more detail. One possibility is to make the fill funnel 2 at the bottom part too small or so tight, that components and/or particles exceeding a predefined size are not enabled to pass. Alternatively, an additional blocking device can be provided, which will be described below.

Figures 4A, 4B, 4C, 4D:
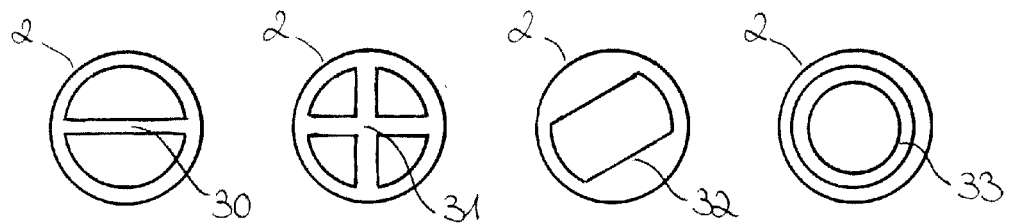
FIGS. 4a to 4d show schematic drawings of a bottom view of fill funnels according to the present disclosure.

FIGS. 4a to 4d show bottom views of a fill funnel 2 having a circular cross-section. In FIGS. 4a to 4c, different embodiments of a blocking device for rendering the fill funnel impermeable to the dyeing device 13 are shown. In FIG. 4a, the blocking device is a bar 30 across the inner side of the fill funnel 2. In the embodiment as shown in FIG. 4b, the blocking device is a cross 31 within the fill funnel 2. In the embodiment shown in FIG. 4c, the blocking device includes two bars 32, noses or wedges protruding from the inner walls of the inner fill funnel 2. FIG. 4d shows an embodiment where a circumferential bar 33 protrudes from the inner walls of the fill funnel 2. The embodiments shown in FIGS. 4a to 4d thus reduce the size and/or the diameter of the fill funnel 2 in such a way, that the fill funnel 2 is rendered selectively impermeable, such that the fill funnel 2 is rendered impermeable to the dyeing device 13 but at the same time permeable to gas and liquid. A further possibility is to provide as a blocking device, a cloth within the fill funnel 2 permeable only to gas and liquid.

The present disclosure is not limited to the shown embodiments of a blocking device. The blocking device only has to fulfill the conditions that it renders the fill funnel 2 selectively impermeable and consequently also selectively permeable to specific components and/or particles, i.e. predefined selected components and/or particles are able to pass the fill funnel 2 and others are blocked.

The blocking device blocks the dyeing device 13 from passing the fill funnel 2, but renders the fill funnel 2 permeable to gas and liquid. Specifically, the blocking device is permeable to water, since water is filled into the chamber 16 through the fill funnel 2. The blocking device is also permeable to gas, since when the water is filled into the suction control chamber 16, air comes out through the fill funnel 2. Additionally, in case that the height 18 of the water 17 within the chamber 16 changes, then air moves out through the opening and the fill funnel 2 in order to avoid an increased pressure within the chamber 16.

Figures 5A, 5B, 5C:
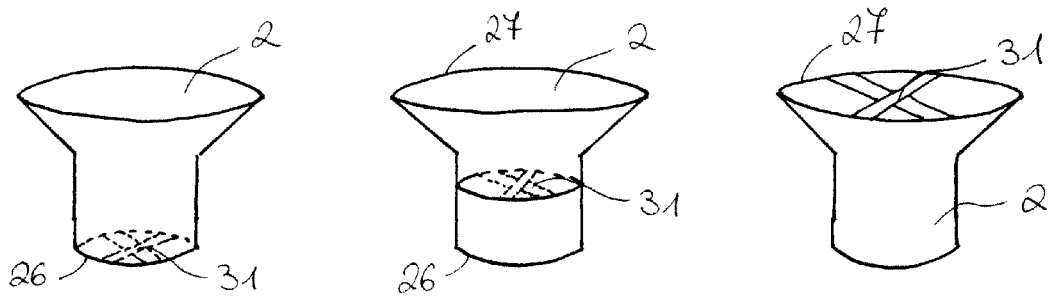
FIGS. 5a to 5c show schematic drawings of different embodiments of a fill funnel according to the present disclosure.

The blocking device is not limited to fill funnels having a circular cross-section but can be used with any type of fill funnel 2. FIGS. 5a to 5c show different embodiments of positioning the blocking device in the fill funnel 2. A cross 31 is shown as blocking device, but it is to be noted that the relative positions can be adapted to any other blocking device. In FIG. 5a, the blocking device 31 is attached to the bottom 26 of the fill funnel 2. In this case, the dyeing device 13 is prevented from entering the fill funnel 2 and will be kept within the chamber 16.

FIG. 5b shows a fill funnel 2 having positioned the blocking device 31 in the middle of the fill funnel 2, i.e. somewhere between the bottom 26 and the top 27. In this case, the dyeing device 13 may enter the fill funnel 2 until it is blocked by the blocking device 31 and afterwards it may fall back into the chamber 16.

FIG. 5c shows a third embodiment of positioning the blocking device 31. In this case, the blocking device 31 is positioned at the top 27 of the fill funnel 2. In this embodiment, the dyeing device 13 could possibly pass through the opening 19 into the fill funnel 2, however when the medical drainage device 1 is correctly positioned in an upward position, the dyeing device 13 will pass through the fill funnel 2 and through the opening 19 back into the chamber 16.

In embodiments, when the fill funnel 2 is attached to the opening 19, no space is left between the fill funnel 2 and casing 11, i.e. the fill funnel 2 is flush with the casing 11. This can, for example, be achieved by providing a fill funnel 2 having a cross-section or shape at least at the bottom part, which corresponds to the shape and cross-section of the opening 19, so that when the fill funnel 2 is attached to the opening 19, no space is left between the fill funnel 2 and casing 11.

The present disclosure is not limited to such an embodiment and covers all other embodiments, where the fill funnel 2 when attached to the opening 19 may leave some parts of the opening 19 uncovered, such that the uncovered openings are small enough to prevent the dyeing device 13 from passing through.

Figures 6A, 6B, 6C:
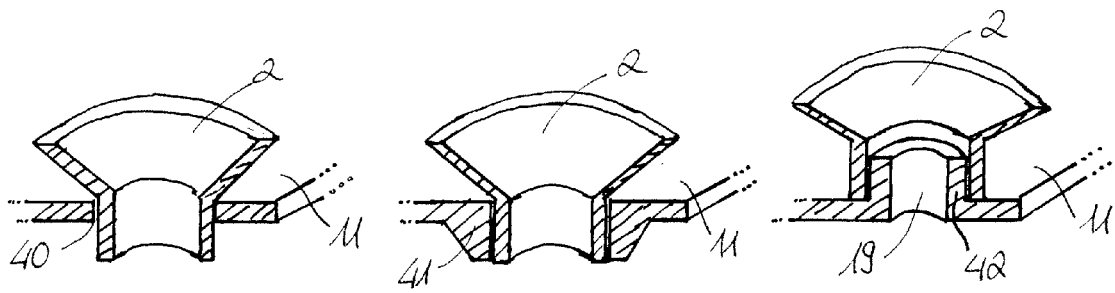
FIGS. 6a to 6c are schematic drawings showing different embodiments of attaching a fill funnel to a medical drainage device according to the present disclosure.

FIGS. 6a to 6c show different embodiments of attaching the fill funnel 2 to the opening 19. A part of the casing 11 is shown having opening 19. As shown in FIG. 6a, the opening 19 can simply be a cut-out in the casing 11 defining borders 40 of the opening 19 within the casing 11. The fill funnel 2 is inserted at least partly into the opening 19 and in embodiments, the fill funnel 2 is flush with the borders 40 of the opening 19. FIG. 6b shows a further embodiment, where within the casing 11 around the opening 19, a nose 41 is provided for providing more stabilisation to the fill funnel 2 when inserted into the opening 19.

FIG. 6c shows an embodiment, where the fill funnel 2 is not inserted into the opening 19, but imposed onto connection means 42 protruding from the casing 11 around the opening 19. The fill funnel 2 is flush with the casing 11 and the connection means 42.

Generally, the fill funnel 2 at the bottom part as shown in FIGS. 6a and 6b can have a size smaller than the opening 19 to be inserted into the opening 19. Alternatively, as shown in FIG. 6c, the fill funnel 2 at the bottom part can have a size larger than the opening 19 and therefore can be imposed onto connection means 42.

In embodiments, the fill funnel 2 is fixedly attached to the opening 19. This can either be accomplished by choosing the sizes of the opening 19 and the fill funnel 2 in such a way, that the fill funnel is kept attached to the casing 11 by friction force such that the space between the fill funnel 2 and the casing 11 is so tight, that the fill funnel 2 is thereby fixedly attached to the opening.

Alternatively or additionally, fixation means can be provided for fixedly attaching the fill funnel 2 to the opening 19 and to the casing 11. Two embodiments of such fixation means are shown in FIGS. 7a and 7b.

Figures 7A, 7B:
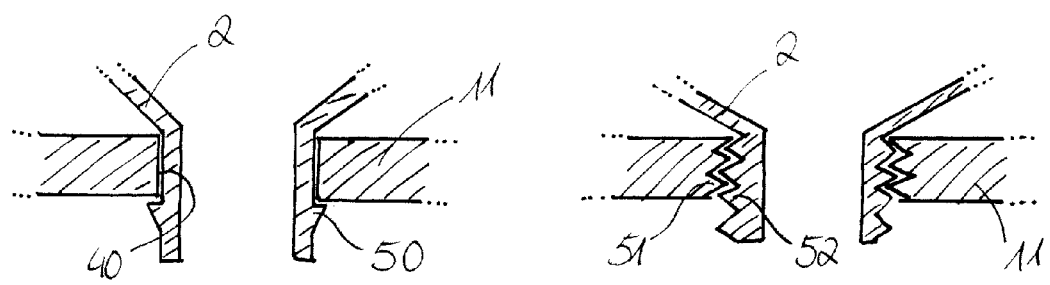
FIGS. 7a and 7b show different embodiments of fixation means according to the present disclosure.

In FIG. 7a, the fill funnel 2 includes wedges 50, which engage with the border 40 of the opening 19. The wedges 50 of the fill funnel 2 are deformable when the fill funnel 2 is inserted into the housing 19 and then after being completely inserted, the wedges 50 will protrude from the fill funnel 2 in such a way, that the fill funnel is fixedly attached to the casing 11.

FIG. 7a shows one possible embodiment, but the present disclosure also includes any other embodiments, where wedges and/or recesses are provided at the fill funnel 2 and/or at the opening 19, and which are adapted to interconnect with each other in such a way, that the fill funnel 2 is fixedly attached to the opening 19.

FIG. 7b shows a further embodiment of fixedly attaching the fill funnel 2 to the casing 11. A screw thread 51, 52 is provided on the fill funnel 2 and on the borders 40 of the opening 19, so that the screw thread 52 of the fill funnel 2 can engage with the screw thread 51 in the casing 11. The fill funnel 2 can thereby be screwed into the opening and fixedly be attached to the opening 19.

It is to be noted that even if the FIGS. 7a and 7b are shown for the cases that the fill funnel 2 is inserted into the opening 19, the described fixation means can also be used in an embodiment as shown in FIG. 6c, where the fill funnel is imposed onto connection means 42 protruding from the casing 11 around the opening 19 from the casing 11.

The present disclosure thus provides a medical drainage device with a fill funnel which makes the handling easier and reduces the numbers of failures or mistakes which may arise during the preparation of the medical drainage device.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A medical drainage device comprising:
   a casing;
   a chamber for indicating the amount of suction applied to an animal or human body by the height of a water column;
   a dyeing device provided within the chamber for dyeing water therein; and
   a fill funnel attached to an opening in the casing for filling water through an opening into the chamber; wherein the fill funnel is configured and dimensioned to be selectively impermeable to the dyeing device and selectively permeable to gas and liquid;
   wherein the fill funnel includes a blocking device for rendering the fill funnel selectively impermeable, and
   wherein the blocking device is a bar across an inner side of the fill funnel.

2. Medical drainage device according to claim 1, wherein the blocking device is a cloth.

3. The medical drainage device according to claim 1, wherein the blocking device is configured and dimensioned to reduce an inner size and a diameter of the fill funnel.

4. The medical drainage device according to claim 1, wherein the blocking device is a cross within the fill funnel.

5. The medical drainage device according to claim 1, wherein the blocking device includes at least one bar protruding from the inner walls of the fill funnel.

6. The medical drainage device according to claim 5, wherein the at least one bar is a circumferential bar.

7. The medical drainage device according to claim 1, wherein the fill funnel is flush with the casing.

8. The medical drainage device according to claim 1, wherein the fill funnel is at least partly inserted into the opening.

9. The medical drainage device according to claim 1, wherein the fill funnel is disposed on connection means protruding from the casing around the opening.

10. The medical drainage device according to claim 1, further comprising a fixation device for fixedly attaching the fill funnel to the casing.

11. The medical drainage device according to claim 1, wherein the chamber is a patient assessment manometer chamber.

12. The medical drainage device according to claim 1, wherein the fill funnel is attached to the medical drainage device by a string.

13. A fill funnel for a medical drainage device, the fill funnel being attachable to an opening in a casing of the medical drainage device for enabling water to fill through the opening into a chamber, wherein the fill funnel includes a blocking device for rendering the fill funnel selectively impermeable, and wherein the blocking device is a bar across an inner side of the fill funnel.

14. A medical drainage device comprising:
   a casing; and
   a chamber for indicating the amount of suction applied to an animal or human body by the height of a water column; and
   a fill funnel attached to an opening in the casing for filling water through an opening into the chamber; wherein the fill funnel includes a blocking device for rendering the fill funnel selectively impermeable,
   wherein the blocking device is a bar across an inner side of the fill funnel.

15. The medical drainage device according to claim 14, wherein the fill funnel is configured and dimensioned to be impermeable to components and particles exceeding a predefined size.

16. The medical drainage device according to claim 14, wherein the fill funnel is configured and dimensioned to be permeable to gas and liquid.

17. The medical drainage device according to claim 1, wherein the fill funnel is configured and dimensioned to be impermeable to components and particles exceeding a predefined size.

* * * * *